United States Patent [19]

Cogliano

[11] 4,306,548

[45] * Dec. 22, 1981

[54] LIGHTWEIGHT POROUS CASTS

[75] Inventor: Joseph A. Cogliano, Baltimore, Md.

[73] Assignee: W. R. Grace & Co., New York, N.Y.

[ * ] Notice: The portion of the term of this patent subsequent to Oct. 21, 1992, has been disclaimed.

[21] Appl. No.: 780,142

[22] Filed: Mar. 22, 1977

[51] Int. Cl.$^3$ .............................................. A61F 5/04
[52] U.S. Cl. ...................................................... 128/90
[58] Field of Search .......................... 128/90; 260/821; 528/483

[56] References Cited

U.S. PATENT DOCUMENTS

| | | | |
|---|---|---|---|
| 935,414 | 9/1909 | Sandmann | 260/821 |
| 1,902,627 | 3/1933 | Elbogen | 128/90 |
| 1,993,277 | 3/1935 | Murphy et al. | 260/821 |
| 2,432,353 | 12/1947 | Talalay | 260/821 |
| 2,576,027 | 11/1951 | Means | 128/90 |
| 2,640,036 | 5/1953 | Brass et al. | 528/483 |
| 2,969,791 | 1/1961 | Ekenstam et al. | 128/90 |
| 3,027,336 | 3/1962 | Gotz et al. | 260/2.5 |
| 3,089,486 | 5/1963 | Pike | 128/90 |
| 3,249,569 | 5/1966 | Fantl | 260/821 |
| 3,375,822 | 4/1968 | Rose | 128/90 |
| 3,421,501 | 1/1969 | Beightol | 128/90 |
| 3,613,675 | 10/1971 | Larsen | 128/90 |
| 3,656,476 | 4/1972 | Swinney | 128/90 |
| 3,745,998 | 7/1973 | Rose | 128/89 R |
| 3,853,124 | 12/1974 | Larson | 128/90 |
| 3,913,298 | 10/1975 | Cogliano | 53/36 |
| 3,968,791 | 7/1976 | Forsberg | 128/90 |
| 4,085,180 | 4/1978 | Stoffey | 128/90 |

FOREIGN PATENT DOCUMENTS 542204 12/1941 United Kingdom ............... 260/821

*Primary Examiner*—C. Fred Rosenbaum
*Attorney, Agent, or Firm*—Howard J. Troffkin

[57] ABSTRACT

This invention relates to a novel process of preparing and applying an orthopedic splint or cast to a broken limb whereby a porous substrate which contains an acid gas coagulable polymer is applied to said limb followed by rigidification of said substrate and polymer through exposure to a coagulating gas.

5 Claims, No Drawings

LIGHTWEIGHT POROUS CASTS

BACKGROUND OF THE INVENTION

Prior Art

Approximately 5,000–6,000 tons/year of calcium sulfate hemihydrate plaster are used for medical support. About 75% of the 4 million casts applied each year in the U.S. are for setting fractures; others are for support of sprained limbs and orthopedic immobilization. These conventional plaster of Paris systems however have many unsatisfactory properties; the casts formed therewith are heavy, X-ray impervious, absorb excessive moisture which has a detrimental effect on the physical properties, are difficult to clean, lack elasticity, are slow to reach ultimate strength, have poor abrasive resistance, and are receptive to bacterial and fungal growth.

There is probably nothing that can be done to overcome all of the problems of wearing a cast, splint, or brace. But through extensive research and development programs the chemical industry is helping to lighten the load and remove some of the inconveniences.

Along the lines of lightening the weight of rigid enclosures and elimination other disadvantages methods have been proposed which utilize polymerizing systems.

The prior art consists essentially of bandages imbued with heat or light curable polymers. As an example of such art U.S. Pat. Nos. 2,576,027, 3,027,336, 3,089,486, 3,421,501, and 3,613,675 may be cited.

Furthermore, more specifically and more closely related to our invention we may also cite U.S. Pat. Nos. 3,375,822, 3,745,998, and 2,969,791.

U.S. Pat. No. 3,375,822 discloses a surgical cast comprising a sealed envelope containing a plurality of low density spheres and a binder material.

U.S. Pat. No. 3,745,998 teaches a cast comprised of a nonporous elastic envelope with an air evacuation tube.

U.S. Pat. No. 2,969,791 teaches an article comprising a woven, open-mesh fabric of textile material. The fabric is dipped in an emulsion of a plastic material including a bonding agent and dried. Just prior to use the thus treated fabric is dipped in or sprayed with a solvent and applied on the body member. The solvent is allowed to evaporate thus causing the applied fabric to rigidify.

In most of these systems however large amounts of liquid volatiles are employed and the increased temperatures required for cure render their use in confined areas undesirable and furthermore high molding temperatures require that an insulating medium be introduced between the curable polymer and the skin which compromises the ability to shape or mold said polymeric layer to the immobilized part satisfactorily.

OBJECT OF THE INVENTION

It is therefore an object of this invention to develop a light weight cast which overcomes the drawbacks of the conventional calcium sulfate casts and at the same time does not present the detrimental effects which characterize the application of most of the lightweight heat or light polymerizable casts.

A further object of the invention is to provide a plastic orthopedic cast which is polymerizable under conditions easily adaptable to those encountered by physicians in the application of plaster of Paris casts.

A still further object of this invention is to provide an orthopedic cast which does not call for application near a source of electrical power.

Other objects will become apparent as the description of this invention proceeds.

BRIEF DESCRIPTION OF THE INVENTION

This invention relates to a novel procedure of preparing and applying a light weight orthopedic cast which does not require application of light or heat energy.

The invention discloses a method of orthopedic cast application wherein substrate is imbued with a gas coagulable polymer and which upon application to a limb followed by exposure to an innocuous gas rigidifies.

DETAILED DESCRIPTION OF THE INVENTION

This invention is based on the property which most latexes possess which is that of particle agglomeration leading to total coagulation upon exposure to gaseous coagulants. U.S. Pat. No. 3,032,524 relates that phenomenon to pH lowering which has a destabilizing effect of latexes and U.S. Pat. No. 3,913,298 applies the gas coagulation effect of latexes in devising a method of packaging.

In the present invention the supra effect is utilized in devising a novel method of applying orthopedic casts.

In practicing the instant invention, expanded nonporous polystyrene foam beads or other shapes, e.g. spaghetti are coated with a layer of neoprene, natural rubber or other latex to give a mixture which can easily be deformed prior to coagulation. The thus coated polystyrene is encased in a porous envelope and said envelope is applied to a broken limb. Additional coated polystyrene is added over the envelope and thereafter a gaseous coagulant, e.g. carbon dioxide is added to gel the latex thus causing the polystyrene beads to adhere to each other thereby producing a unified, rigidized structure.

The coating of the beads can be done in various conventional ways. For example the beads can be charged to a rotating hopper along with sufficient latex to coat the beads. Since the beads are non-porous, this system is economical since it is not necessary to fill up the pores of the beads with latex before a coating on the beads, sufficient to form a rigidized structure, is obtained.

The amount of latex added to the beads is dependent upon bead diameter. That is, the smaller the bead diameter the more latex is necessary due to the greater surface area of the beads. Ordinarily amounts from 1 to 5 parts of latex to one part of beads by weight, preferably 1 to 3 parts of latex to one part of beads by weight is employed to coat the expanded polystyrene. Excess latex is to be avoided since it merely drips off the beads forming highly concentrated areas of latex in the container.

The latexes employed in the instant invention are those well known latexes which can be coagulated by a gaseous coagulant. Anionic neoprene latex is preferred but other latexes are operable. Such latexes include but are not limited to cationic neoprene, natural rubber, synthetic rubber, and the like. In the event that the latex is in a highly stabilized condition it is possible to add well known commercially available reactants thereto to bring it to a point of incipient gelation prior to coating the non-porous material.

Various gaseous coagulants can be employed herein to coagulate the latex. Preferred gaseous coagulants are those which are non-corrosive, non-toxic and non-irritating such as carbon dioxide. However other gaseous coagulants such as $SO_2$, $SO_3$, $NO$, $NO_2$, formic, acetic, propionic, or halogenated acids can also be employed.

The coagulation step herein is carried out under ambient conditions, i.e. 60°–110° F., at atmospheric pressure. Ordinarily, the coagulation step is performed at room temperature, about 70°–75° F., at atmospheric pressure.

The non-porous foamed material employed herein is preferably expanded polystyrene due to its economics, availability and light weight. The expanded polystyrene usually has a density in the range of about 0.1 to 7 pounds per cubic foot. Other suitable materials include phenol-formaldehyde foam beads, polyurethane foam beads, fiber glass mats, or woven cotton sheets.

Preferred porous envelopes include open-mesh fabrics such as cotton gauze, cotton crinoline and other natural and synthetic bandage materials well known to those skilled in the art. For example the carrier may be a cotton gauze having 10–50 warp and 10–50 weft threads to the square inch, some or all of the threads optionally being resilient or elastic.

The porous envelope may also either be woven or non-woven and may also be manufactured in whole or part from plastic or glass fibers. The plastics may include, for example, polyethylene, polypropylene and various polyester or polyamide fibers, e.g. Dacron, nylon, and the like.

The porous envelope may also be prepared from porous foams such as polyether polyurethane and polyester foams. Other materials will be apparent to those skilled in the art in the light of the present disclosure.

In practicing the instant invention it is desirable to know when coagulation is complete. Aside from merely feeling the rigid structure, another method which can be employed is the inclusion of a pH indicator in the system. Such indicators are well known and available commercially.

The following examples while in no way intended to be limiting, will aid in the understanding of this invention.

EXAMPLE 1

172.4 grams of expanded polystyrene foamed beads having an average density of 2 pounds per cubic foot were coated with 344.8 grams of an anionic neoprene latex "L-572" (50 percent solids) commercially available from E. I. Dupont by admixing the beads and the latex in a plastic bag manually until the coating was uniform. After mixing, a portion of the mixture was placed in a plastic lined cardboard box. An object simulating a limb was placed in the box and covered with the additional portion of the coated expanded polystyrene beads. Carbon dioxide was charged to the box in an amount sufficient to coagulate the latex. After 5 minutes the latex coagulated thereby forming a lightweight, rigidized, unified structure of the beads around said object in the box.

EXAMPLE 2

Two parts by weight of neoprene latex "L-572" was mixed with 1 part by weight of expanded polystyrene foamed beads and charged to two perforated bags. Perforations in the bags were of such size as to allow the passage of a gas but not large enough to pass the expanded polystyrene beads. The two bags were placed on the bottom of a plastic container and two cylindrically shaped objects simulating limbs were recessed in the deformable bags and carbon dioxide was added to each of the bags. After 5 minutes coagulation occured in each of the bags forming a unified rigid lightweight structure in each bag similar to the structure outside of perforated bags formed in the cardboard box in Example 1.

EXAMPLE 3

⅛ to ¼ inch polystyrene foam beads were wetted with an anionic neoprene latex "L-572". The pellets were encased in a 2 inch tubular gauze (Scholl Mfg. Co. "Tubegauz") and wrapped around a beaker (to simulate a limb) in 2 to 3 layers. The sample was placed in a container and carbon dioxide passed over it. About 10 minutes later the sample had rigidified.

EXAMPLE 4

A fiber glass mat was wetted with neoprene latex as above and wrapped around a paper cup. After contact with carbon dioxide said mat was removed and maintained its rigidified circular shape.

EXAMPLE 5

A woven fiber glass mat and also a woven cotton sheet were treated as in Example 4. After exposure to carbon dioxide they rigidized upon removal from the simulated limb retained their shape.

What is claimed is:

1. A process of preparing and applying a lightweight orthopedic cast which comprises enclosing a filler material coated with an acid gas coagulable polymer in a porous envelope, placing an affected limb requiring orthopedic immobilization in contact with said envelope, orthopedically immobilizing said affected limb by wrapping said envelope around said affected limb requiring orthopedic immobilization and exposing said polymer coating to a gaseous coagulant until said wrapping forms a solid, rigid, orthopedic cast.

2. The process according to claim 1 wherein said filler material is wetted with said acid gas coagulable polymer.

3. The process according to claim 1 wherein the acid gas coagulable polymer is a neoprene latex and wherein the gaseous coagulant is carbon dioxide.

4. The process according to claim 1 wherein said filler material may be selected from the group comprised of polystyrene foam beads, phenol-formaldehyde foam beads, polyurethane foam beads, fiber glass mats or woven cotton sheets.

5. The process according to claim 1 wherein the gaseous coagulant is carbon dioxide.

* * * * *